(12) United States Patent
Alqudah

(10) Patent No.: US 9,038,637 B2
(45) Date of Patent: May 26, 2015

(54) DEVICE FOR PREVENTING ASPIRATED SUBSTANCE FROM GOING INSIDE THE LUNGS AND ENABLING SPEAKING

(71) Applicant: Mohammad Alqudah, Elmwood Park, NJ (US)

(72) Inventor: Mohammad Alqudah, Elmwood Park, NJ (US)

(73) Assignee: Houd Alqudah, Elmwood Pard, NJ (US)

( * ) Notice: Subject to any disclaimer, the term of this patent is extended or adjusted under 35 U.S.C. 154(b) by 191 days.

(21) Appl. No.: 13/872,111

(22) Filed: Apr. 28, 2013

(65) Prior Publication Data

US 2013/0340748 A1    Dec. 26, 2013

Related U.S. Application Data

(60) Provisional application No. 61/663,518, filed on Jun. 22, 2012.

(51) Int. Cl.
*A61M 16/00* (2006.01)
*A61M 16/04* (2006.01)

(52) U.S. Cl.
CPC ....... *A61M 16/0468* (2013.01); *A61M 16/0497* (2013.01); *A61M 16/0463* (2013.01); *A61M 16/044* (2013.01); *A61M 16/0477* (2014.02)

(58) Field of Classification Search
CPC ............ A61M 16/0468; A61M 16/04; A61M 16/0497; A61M 16/0463; A61M 16/044
USPC ............................ 128/207.14–207.16, 200.26
See application file for complete search history.

(56) References Cited

U.S. PATENT DOCUMENTS

| | | | | |
|---|---|---|---|---|
| 5,464,011 A | * | 11/1995 | Bridge | 128/207.14 |
| 5,957,978 A | * | 9/1999 | Blom | 623/9 |
| 6,722,367 B1 | * | 4/2004 | Blom | 128/207.14 |
| 2012/0103342 A1 | * | 5/2012 | Shikani et al. | 128/207.16 |

* cited by examiner

*Primary Examiner* — Kristen Matter

(57) ABSTRACT

A device for preventing aspirated substance from going inside lungs of a patient and enabling speaking. The device comprises an outer tube, an inner tube, an inner tube opening in the inner tube to allow air to travel from the inner tube to the outer tube, an outer tube opening in the outer tube to allow air to escape out of the device, a valve disposed on the outer tube opening, which allows the air to escape out of the device to the trachea of the patient while exhaling, such that the valve closes by gravity and prevents any material to go inside the device from the outer tube opening and a inflatable cuff disposed around the inner end of the outer tube.

7 Claims, 4 Drawing Sheets

DEVICE FOR PREVENTING ASPIRATED SUBSTANCE FROM GOING INSIDE THE LUNGS AND ENABLING SPEAKING

CROSS-REFERENCE TO RELATED APPLICATIONS

This application claims the benefit of U.S. Provisional Application Ser. No. 61/663,518, filed on Jun. 22, 2012, the entire content of which is hereby incorporated by reference.

FIELD OF THE INVENTION

The present invention relates generally to a device for aiding patients who have dysphagia, and more particularly to a device which prevents aspirated substance from going into the lungs and at the same time enable the patient to speak.

BACKGROUND OF THE INVENTION

Dysphagia is the medical term for the symptom of difficulty in swallowing. It is a sensation that suggests difficulty in the passage of solids or liquids from the mouth to the stomach, a lack of pharyngeal sensation, or various other inadequacies of the swallowing mechanism. Individuals with difficulty swallowing may find liquids cause coughing, choking, so for such patients thickening drinks, puree, soft food enables them to swallow safely. Individuals suffering from dysphagia are often ordered onto thickened fluids and sometimes even not to eat completely by mouth based on severity of the problem. The thicker consistency makes it less likely that an individual with dysphagia will aspirate while they are drinking.

Swallowing disorders can occur in all age groups, resulting from congenital abnormalities, structural damage, and/or medical conditions. Swallowing problems are a common complaint among older individuals, and the incidence of dysphagia is higher in the elderly in patients who have had strokes, and in patients who are admitted to acute care hospitals or chronic care facilities. Other causes of dysphagia include head and neck cancer and progressive neurologic diseases like Parkinson's disease, Dementia, Multiple sclerosis, Multiple system atrophy, or Amyotrophic lateral sclerosis.

The consequences of pulmonary aspiration ranges from no injury at all, to chemical pneumonitis or pneumonia, to death within minutes from asphyxiation. These consequences depend on the volume, chemical composition, particle size, presence or absence of infectious agents and underlying health status of the person.

Another related situation with patients who have serious breathing problems or are on ventilator, tracheostomy tubes are used to provide an airway or gas ventilation path directly to the patient's trachea through a surgically made opening in the throat. In order to cause minimal trauma to the patient, the opening into the trachea is preferably made just large enough to accommodate the tube. This can make insertion of the tube through the opening difficult, since it must be pushed through resilient cartilage. Obturators can be used to provide the tube with additional stiffness and to prevent entry of tissue into the patient end of the tube. Such obturators do not significantly help insertion since they only project from the patient end by a maximum distance about equal to the internal diameter of the tube.

FIG. 1 illustrates a schematic view showing prior art tracheostomy tube installed into the trachea of a patient. As seen the air when inhaled from the nasal cavity goes through the trachea and reaches the lungs. But patients who have breathing problems the passage is blocked and a tracheaostomy tube is required. The tracheostomy tube provides an alternative passage for the air to enter and exit from the human body. In case of patients having dysphagia at least some portion of the food and liquids material taken from the mouth goes towards the trachea instead of its normal path through esophagus. This causes the food and liquid particles to go to the lungs causing trouble in breathing for the patient.

The tracheostomy tube allows the patient to breathe but the patients ventilated via a tracheostomy have assisted laryngeal speech. Laryngeal speech has been accomplished by partially deflating the cuff of the tracheostomy tube, allowing a minimal air leak around the cuff and through the larynx during the lung filling phase of ventilation. Although this technique does result in speech, the speech is intermittent and the voice is not loud enough because the air gets dispersed between two paths, first through the vocal cords and second through the tracheostomy. A speaking valve may also be used to prevent the air to leak air from the tracheostomy and redirect the exhaled air to go through the vocal cords for better phonation. The patients who suffer from dysphagia and have tracheostomy tube installed may also have problem of aspiration.

To date, there are no available effective methods and devices to stop the aspirated contents to go into the lung and at the same time keeping the ability of phonations and speaking. Several devices were invented to decrease or stop aspirated content to pass into the lungs; however none of these inventions able to help the patients who have swallowing difficulties to keep the functions of breathing and speaking and prevent the aspirated contents to go into the lungs completely at same time. For example U.S. Pat. No. 7,856,983 discloses an Apparatus for assisting phonation in a wearer of a tracheostomy tube having a first end lying outside the trachea of the wearer in the use orientation, a second end lying inside the trachea of the wearer in the use orientation, and a first lumen coupling the first and second ends of the tracheostomy tube. The tracheostomy tube may or may not include a fenestration through a sidewall of the tracheostomy tube coupling the first lumen to the outside of the tracheostomy tube. The apparatus includes a cannula for insertion into the first lumen from the first end of the tracheostomy tube. The cannula includes a first end lying outside the first end of the tracheostomy tube in the use orientation, a second, opposite end, and a second lumen coupling the first and second ends of the cannula. If the tracheostomy tube has a fenestration, the second end may lie within the first lumen adjacent and toward the first end of the tracheostomy tube from the fenestration, or generally between the first end of the tracheostomy tube and the fenestration, or adjacent the second end of the tracheostomy tube. A one-way valve is provided at the second end of the cannula. The one-way valve remains open during inhalation, allowing air to enter the lungs. While exhaling, the valve closes.

The speaking valve devices, such as the Passy-Muir speaking valve (PMV) enables phonation and improves communication by redirecting the air flow through the vocal folds, mouth and nose. Studies have shown that the passy-muir speaking valve offers patients numerous clinical benefits beyond communication. Benefits include facilitating swallowing by increasing the pharyngeal pressures needed to move the food bolus down the pharynx into the esophagus. Some studies report that when aspiration was not eliminated, it was reduced using a passy-muir speaking valve. However, studies have shown that this reduction was not quantifiably measured.

U.S. Pat. No. 5,957,978 discloses a tracheotomy tube which comprises a first port for orienting outside the neck of a wearer, a second port for orienting within the trachea of the wearer, and a passageway connecting the first and second ports to permit the flow of gases from the first port to the second port on inhalation by the wearer and from the second port to the first port on exhalation by the wearer. The tracheotomy tube further comprises a third port oriented between the first and second ports, and a valve controlling flow through the third port. The valve opens to permit flow from the passageway through the third port.

The speaking valves used with cuffless or deflated tracheostomy tube or with fenestrated tracheostomy tube, so the redirected airs flow through the vocal folds, mouth and nose through the fenestration and/or around the deflated tube. Fenestrations refer to the holes in the lumen of the tracheostomy tube. These can be several small holes or one large hole. Airflow can be directed either via the tracheostomy tube (using a non-fenestrated inner lumen) or partially via the upper airway and tracheostomy tube (using the fenestrated inner or outer lumen). If the fenestrated inner lumen is inserted whilst the cuff is deflated it allows patients to breathe through the fenestration of the tracheostomy tube as well as around it. This may improve the patient's ability to vocalize. However, it may create an opportunity for the aspirated contents in patients who have swallowing difficulties to enter the lungs through the fenestration and around the deflated cuff. Basically using the fenestrated tube in patients who have swallowing disorder put them under the risk of aspiration, the holes in the tube will give the chance for aspirated contents.

Similarly U.S. Pat. No. 6,840,242 discloses a tracheostomy aspiration suction tube for management of tracheostomized patients with co-existing dysphagia allowing aspirated material to be collected and removed from the patient prior to traveling toward the lungs. The tracheostomy aspiration suction tube utilizes a primary cannula as a passageway for air to the patient's lungs, while also providing an insertion cannula capable of receiving an inflatable collection receptacle to be placed below the vocal cords. Upon inflation, the collection receptacle forms a seal with the patient's trachea, which effectively catches any aspirated material. Attached to the collection receptacle is a drainage tube connected an external suction device. The aspirated material is suctioned out of the collection receptacle and away from the patient. The collection receptacle can be removed and reinserted as needed.

The prior art teaches systems and methods for management of tracheostomized patients with co-existing dysphagia allowing aspirated material to be collected and removed prior to travelling toward the lungs, but the patients are not able to speak during the use of this device. The prior art also teaches tracheostomy devices which also allow speaking but the speech is intermittent.

In view of the limitations inherent in the available devices, there exists a need for an improved device which prevents aspirated substance from going into the lungs and same time will enable the patient to speak and the device is capable of overcoming disadvantages inherent in conventional devices in a cost effective, secure, and environmental friendly manner. The present invention fulfils this need and provides further advantages as described in the following summary.

SUMMARY OF THE INVENTION

In view of the foregoing disadvantages inherent in the prior arts, the general purpose of the present invention is to provide an improved combination of convenience and utility, to include the advantages of the prior art, and to overcome the drawbacks inherent therein.

The main objective of the present invention is to prevent food, liquids, acid reflux and secretions to go into the lungs in patients who have swallowing difficulties. At the same time, it also allows the air to go up through the vocal folds, mouth and nose for speaking. This multifunction device can also work as a tracheostomy tube, so it can be used for the patients who have dysphagia and present with need of using a tracheostomy tube for breathing as well.

In one aspect, the present invention provides a device for preventing aspirated substance from going inside a lung of a patient and enabling speaking. The device comprises an outer tube, an inner tube, an inner tube opening in the inner tube to allow air to travel from the inner tube to the outer tube, an outer tube opening in the outer tube to allow air to escape out of the device, a valve disposed on the outer tube opening, which allows the air to escape out of the device to the trachea of the patient while exhaling, such that the valve closes by gravity and prevents any material to go inside the device from the outer tube opening and a inflatable cuff disposed around the inner end of the outer tube.

In another aspect the present invention, the device further includes a suction tube disposed over the outer tube surface enabling sucking of the aspirated substance from the device.

These together with other aspects of the invention, along with the various features of novelty that characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there are illustrated exemplary embodiments of the invention.

BRIEF DESCRIPTION OF THE DRAWINGS

The advantages and features of the present invention will become better understood with reference to the following more detailed description taken in conjunction with the accompanying drawings in which.

Like reference numerals refer to like parts and steps throughout the several views of the drawings.

DETAILED DESCRIPTION OF THE DRAWINGS

In the following description, for purposes of explanation, numerous specific details are set forth in order to provide a thorough understanding of the present invention. It will be apparent, however, to one skilled in the art that the present invention may be practiced without these specific details.

Figure 1:
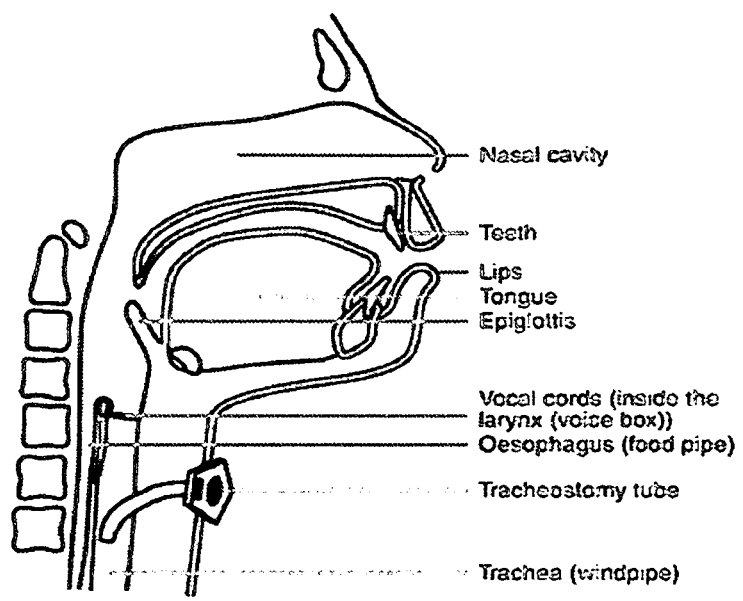
FIG. 1 illustrates a schematic view showing prior art tracheostomy tube installed into the trachea of a patient.
Figure 2:
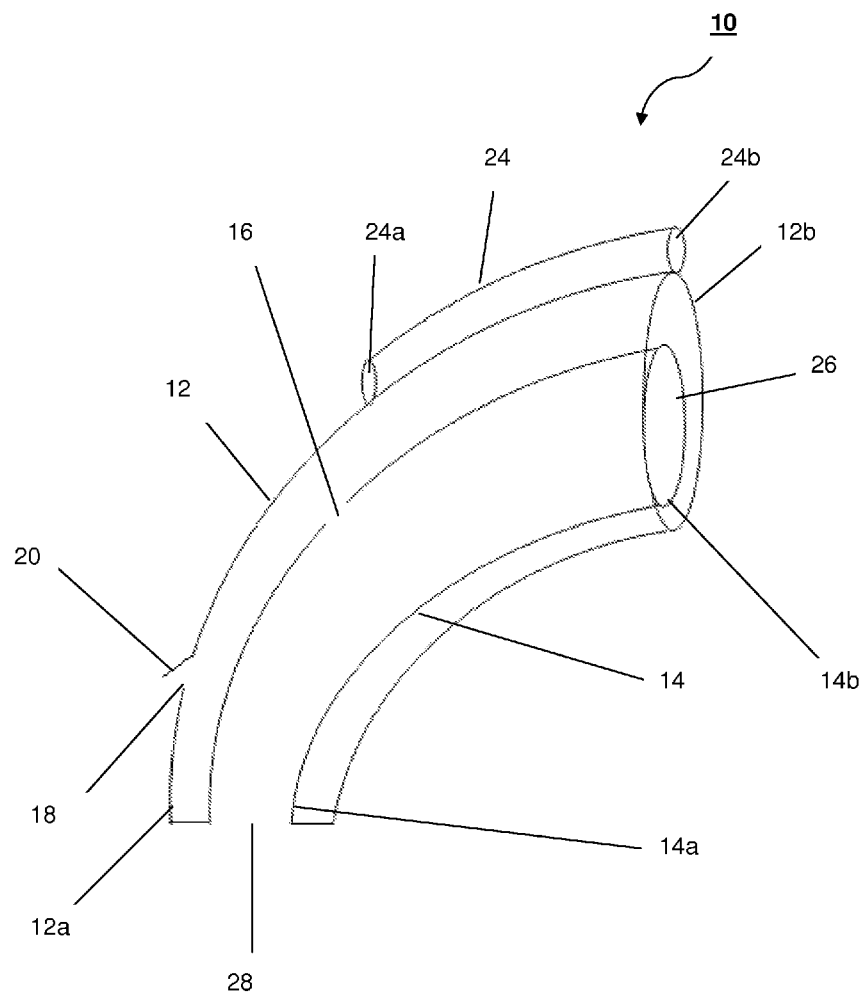
FIG. 2 illustrates a schematic view of the device, according to one embodiment of the present invention.
Figure 3:
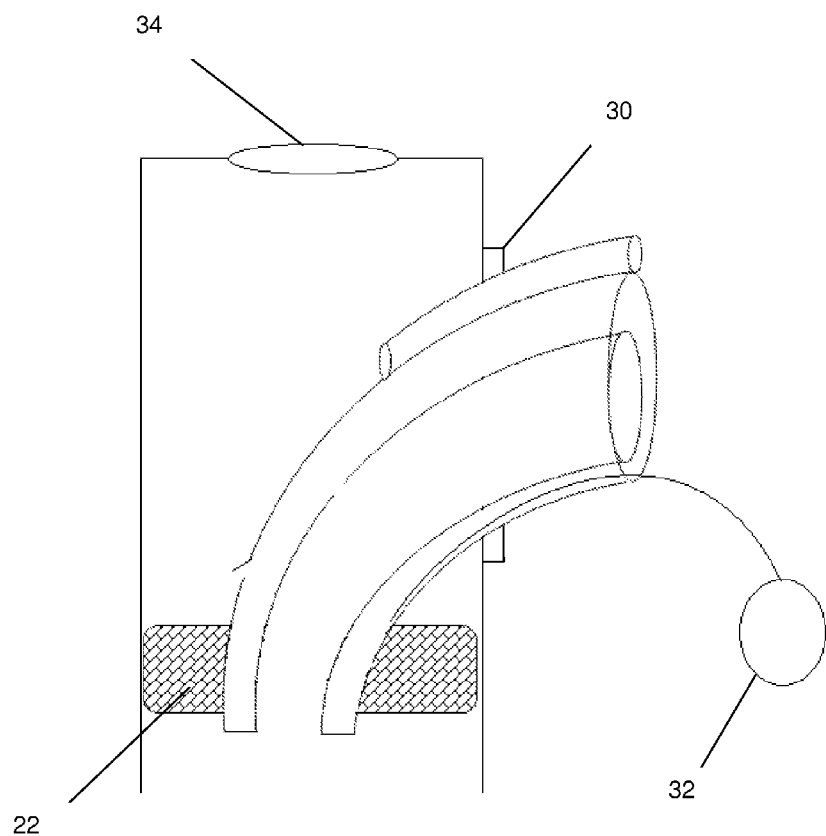
FIG. 3 illustrates a sectional view of the device installed in the trachea of a patient, according to one embodiment of the present invention.

Referring to FIGS. 2 and 3, which illustrate a schematic view of the device for preventing, aspirated substance from going inside lungs of a patient and enabling speaking, according to one embodiment of the present invention. The device 10 comprises an outer tube 12 having an inner end 12a and an outer end 12b, such that the inner and outer ends are inside and outside a trachea of the patient respectively, an inner tube 14 having an inner end 14a and an outer end 14b, such that the outer end 14b is outside the trachea of the patient and receives air from outside and the inner end 14a is inside the trachea of the patient and directs the air inside the trachea, an inner tube opening 16 in the inner tube 14 to allow air to travel from the inner tube to the outer tube 12, an outer tube opening 18 in the outer tube to allow air to escape out of the device 10, a valve 20 disposed on the outer tube opening 18 which allows the air to escape out of the device to the trachea of the patient while exhaling, and an inflatable cuff 22 disposed around the inner end 12a of the outer tube.

The air enters the device 10 from opening 26 when the patient inhales. The air travels through the inner tube 14 and then reaches to the trachea of the patient from the opening 28. The force and speed of the travelling air is strong enough to prevent any major leakage of air from the inner tube opening 16. A suction pump may be used for sucking the aspirated substance from the device 10. The inner ends 12a and 14a of the outer and inner tubes respectively are joined, which leaves some space between the two tubes.

The device 10 is installed in the trachea of the patient from a tracheal button 30 as shown in FIG. 3. The device 10 helps the patient having breathing problem by providing the alternate passage to breathe. The device 10 further includes an inflating pump 32 for inflating and deflating the inflatable cuff 22 as per the requirements.

When the patient inhales the valve 20 disposed on the outer tube opening 18 remains closed when the patient inhales and opens when the patient exhales. The valve 20 closes by itself by the force of gravity and only opens by the pressure of exhaled air. When the patient exhales air travels through the inner tube opening 16 and escapes out through the valve 20 into the trachea of the patient. The air travels to the vocal folds 34 for phonation and speaking. In one embodiment the device 10 includes a speaking valve (not shown) disposed on the outer end 12b of the outer tube such that the speaker valve opens when the patient inhales and closes when the patient exhales. When the patient inhales and air is received from the opening 26, the speaker valve is opened and allows air to come inside without any obstruction. On the other hand when the patient exhales the speaker valve closes the opening 26 and does not allow the exhaled air to go out from the opening 26. Since the speaking valve is closed, the exhaled air is forced to escape from the inner tube opening 16 and then from the outer tube opening 18. This makes air to travel through the vocal cords 34 enabling the patient to speak.

The openings 16 and 18 have dual purpose, first they channelize the escape of air through the vocal chords 34 and secondly they play a crucial role in preventing any aspirated substance to go inside a lung of the patient.

When some food material accidently travels to the trachea instead of esophagus, it is prevented from entering the lungs by the inflated inflatable cuff 22. The inflatable cuff 22 when inflated, surrounds the inner end 12a of the outer tube and seals the space between the device 10 and inner portion of trachea, thereby creating a barrier for any foreign substance to go inside the lungs. The aspirated material sets over the inflatable cuff from where it can be removed. The inflatable cuff 22 has to be deflated by using the inflating pump 32 when the device 10 needs to be removed from the trachea of the patient. So if the aspirated material is present over the inflatable cuff 22, and it is deflated then the aspirated material may fall inside the trachea and reach the lungs of the patient.

In one embodiment of the invention the device 10 further includes a suction tube 24 disposed over the outer tube 12 surface enabling sucking of the aspirated substance from the device 10. The suction tube 24 has an inner end 24a and an outer end 24b, such that the inner and outer ends are inside and outside a trachea of the patient respectively. A suction pump (not shown) may be used to suck the aspirated material gathered on the inflatable cuff 22 through the suction tube 24.

It may be possible that the quantity of aspirated material is more and it may form a heap which reaches above the outer tube opening 18, and from there enter into the device and then to the lungs of the patient. However such possibility is prevented by the valve 20 which closes by gravity. Even if some aspirated material gets inside the device 10 through the outer tube opening 18, it accumulated in the space between the walls of the inner tube 14 and the outer tube 12. In one embodiment the inner tube opening 16 is located higher than the outer tube opening 18, such that when the inner tube is fully inserted into the outer tube, a central axis of the inner tube opening is offset from a central axis of the outer tube opening such that the outer tube opening is located more proximally to the inner ends of the inner and outer tubes than the inner tube opening, which prevents the aspirated material to enter into the inner tube 14 and then go towards lungs from the opening 28.

Figure 4:
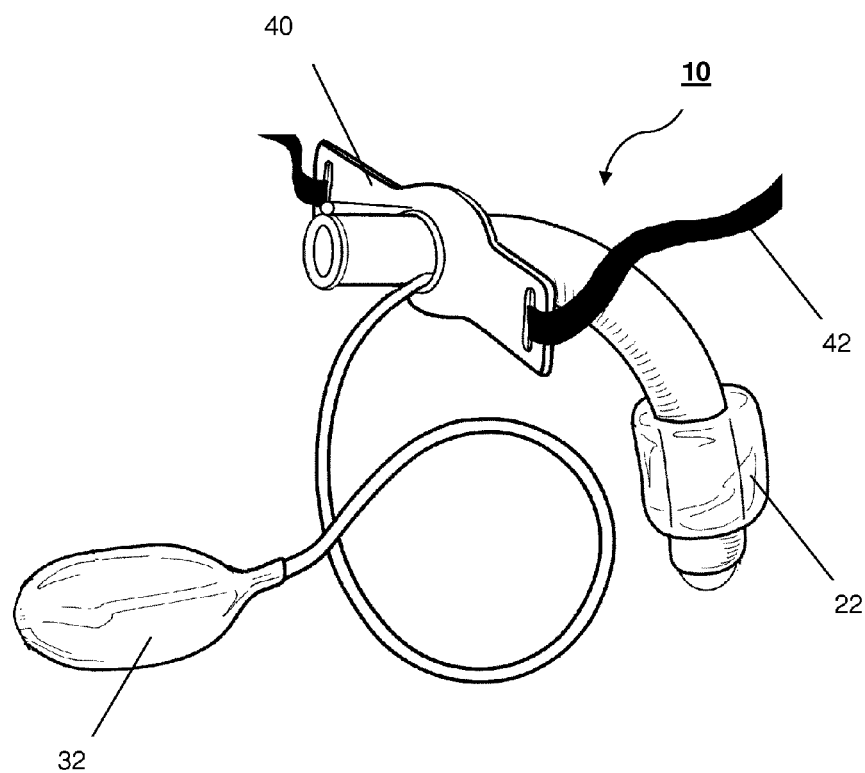
FIG. 4 illustrates a schematic view of the device with neck flange, according to one embodiment of the present invention.

The device 10 is installed in the trachea of the patient from a stoma in the patient's neck. A tracheal button 30 is also fitted in the stoma to provide support to the device 10. In one embodiment the device 10 may include a neck flange 40 as shown in FIG. 4. The neck flange 40 may fit over the tracheal button 30 and then the device 10 may be inserted into the trachea of the patient. After the inside ends 12a and 14a reaches in the trachea to desired position, the inflatable cuff 22 is inflated using the inflating pump 32.

The device 10 of the present invention is a multifunction device and can also be used with patients who have dysphagia and also need to use tracheostomy tube to help in breathing. Basically the device 10 is designed to allow the air to go up through the vocal cords for phonation and at the same time prevents the aspirated content to go into the lungs.

The diameter of the outer tube 12 is smaller than the tracheal button 30 or the size of the stoma, so that it can be easily inserting into the trachea and in taking out. The aspirated food, liquids, and secretions that passed the level of the vocal folds 34 will not go down to the lungs, it will accumulate on the surface of the cuff 22 and will not pass into the lungs.

Therefore, the aspirated materials remains on top of the cuff and will not travel downward toward the lungs by gravity when the cuff is deflated. The device 10 also has a hole 50 between the inner tube 14 and the outer tube 12, so it will allow suctioning any aspirated material that gets accumulated in the gap between the outer and inner tube 12 and 14.

The ability to suck, remove and clean the device 10 may reduce the risks for bacterial colonization on the device. Patients with dysphagia may use this device during oral intake. The device 10 may be removed and any aspirated materials that are caught by the device can be cleaned. If the patient has a good cough reflux, the force of cough reflux will be able to cough the aspirated materials and clear the airway. The aspirated content may be sucked out from the suction tube 24, while the device 10 is installed in patients who need the tracheostomy to support breathing. Patients with dysphagia who need tracheostomy tubes may use this device for more functions including swallowing and speaking while using the tracheostomy tube. Patients with Gastroesophageal reflux disease (GERD), who already has tracheostomy or tracheal button can use this device during sleep when the gravity is not in effect and the risk of aspiration with acid reflux is high.

Speech language pathologists can use this device to diagnose and treat swallowing disorders. During diagnosis, the speech language pathologist will be able to see the amount of food and liquids that passed the level of vocal cords 34 and pooled above the device during the suctioning or when pulling out the device. This device also helps in treating the swallowing disorder by giving the patients an opportunity to try different consistencies of food and liquids without being worried of consequences of aspiration. The present device can also be used as a long term solution for patients with severe swallowing disorders, who did not progress through the swallowing treatment conducted by the speech therapist.

Although a particular exemplary embodiment of the invention has been disclosed in detail for illustrative purposes, it will be recognized to those skilled in the art that variations or modifications of the disclosed invention, including the rearrangement in the steps of the method, changes in sequence, variations in steps may be possible. Accordingly, the invention is intended to embrace all such alternatives, modifications and variations as may fall within the spirit and scope of the claims of the present invention.

The exemplary embodiments described herein detail for illustrative purposes are subject to many variations of structure and design. It should be emphasized, however that the present invention is not limited to particular device for preventing aspirated substance from going inside a lung of a patient and enabling speaking, as shown and described. Rather, the principles of the present invention can be used with a variety of configurations and arrangements of devices for preventing aspirated substance from going inside a lung of a patient and enabling speaking. It is understood that various omissions, substitutions of equivalents are contemplated as circumstances may suggest or render expedient, but the present invention is intended to cover the application or implementation without departing from the spirit or scope of the claims.

As used in this application, the words "a," "an," and "one" are defined to include one or more of the referenced item unless specifically stated otherwise. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is understood that various omissions, substitutions of equivalents are contemplated as circumstance may suggest or render expedient, but is intended to cover the application or implementation without departing from the spirit or scope of the claims of the present invention.

What is claimed is:

1. A tracheostomy aspiration device for preventing aspirated substance from going inside a lung of a patient and further assisting phonation, the tracheostomy aspiration device comprising:

an outer tube having an inner end, an outer end, and a wall extending from the inner end to the outer end, such that the inner end and the outer end are adapted to be placed inside and outside a trachea of the patient respectively, when in use;

an inner tube having an inner end, an outer end, and a wall extending from the inner end to the outer end, such that the outer end is adapted to be placed outside the trachea of the patient and receive air from an outside environment, and the inner end is adapted to be placed inside the trachea of the patient to direct the air inside the lung of the patient, wherein the inner tube is disposed inside the outer tube, such that a gap is left in between the inner tube and the outer tube;

an inner tube opening in the wall of the inner tube to allow the air to travel from the inner tube to the gap while the patient is exhaling;

an outer tube opening in the wall of the outer tube to allow the air to escape from the gap to the trachea of the patient;

a valve disposed on the outer tube opening, allowing the air to escape out from the gap to the trachea of the patient while the patient is exhaling, further the valve is adapted to close by gravity while the patient is inhaling and prevent the aspirated substance to go inside the lung from the outer tube opening; and a inflatable cuff disposed around the inner end of the outer tube to create a barrier for the aspirated substance from going inside the lung of the patient and further accumulates the aspirated substance on the inflatable cuff, wherein when the inner tube is fully inserted into the outer tube, a central axis of the inner tube opening is offset from a central axis of the outer tube opening such that the outer tube opening is located more proximally to the inner ends of the inner and outer tubes than the inner tube opening.

2. The tracheostomy aspiration device according to claim 1, further comprising a suction tube configured with the outer end of the outer tube enabling sucking of the aspirated substance accumulated on the inflatable cuff; the suction tube having an inner end and an outer end, such that the inner end and outer end are adapted to be placed inside and outside the trachea of the patient respectively.

3. The tracheostomy aspiration device according to claim 1, further comprising a suction pump for sucking the aspirated substance accumulated on the inflatable cuff through a suction tube.

4. The tracheostomy aspiration device according to claim 1, further comprising a tracheal button for securing over the outer end of the outer tube to lockingly engage the outer tube.

5. The tracheostomy aspiration device according to claim 1, further comprising an inflating pump for inflating and deflating the inflatable cuff.

6. The tracheostomy aspiration device according to claim 1, further comprising a speaker valve disposed on the outer end of the outer tube, wherein the speaker valve is adapted to open when the patient inhales to allow the air to come inside the inner tube without any obstruction and the speaker is valve adapted to close the outer end of the inner tube when the patient exhales to prevent the exhaled air from going out through the outer end of the inner tube.

7. The tracheostomy aspiration device according to claim 1, wherein while in use and the patient is exhaling the air escapes through the valve and goes towards a vocal cord of the patient to assist phonation.

* * * * *